US006850889B1

(12) United States Patent
Zayas, Jr.

(10) Patent No.: US 6,850,889 B1
(45) Date of Patent: Feb. 1, 2005

(54) SYSTEM AND METHOD FOR CONDUCTING A PHYSICIAN-PATIENT CONSULTATION

(75) Inventor: Robert Zayas, Jr., Houston, TX (US)

(73) Assignee: Internet Treatment Consulting, N.V. (NL)

( * ) Notice: Subject to any disclaimer, the term of this patent is extended or adjusted under 35 U.S.C. 154(b) by 453 days.

(21) Appl. No.: 09/590,920

(22) Filed: Jun. 9, 2000

(51) Int. Cl.$^7$ ............................................. G06F 17/60
(52) U.S. Cl. ............................ 705/3; 705/4; 600/301
(58) Field of Search ................ 705/2–4; 600/300–301; 725/24

(56) References Cited

U.S. PATENT DOCUMENTS

| | | | |
|---|---|---|---|
| 5,724,580 A | * | 3/1998 | Levin et al. ............. 707/104.1 |
| 5,827,180 A | * | 10/1998 | Goodman ................... 600/300 |
| 5,867,821 A | | 2/1999 | Ballantyne et al. ............ 705/2 |
| 5,911,687 A | * | 6/1999 | Sato et al. ................... 600/300 |
| 5,950,630 A | * | 9/1999 | Portwood et al. ........... 128/897 |

(List continued on next page.)

FOREIGN PATENT DOCUMENTS

| | | | | |
|---|---|---|---|---|
| JP | 2000271147 A | * | 10/2000 | ........... A61B/19/00 |
| JP | 2001306691 A | * | 11/2001 | ........... G06F/17/60 |
| JP | 2001309891 A | * | 11/2001 | ............ A61B/5/00 |

OTHER PUBLICATIONS

Computerized Case Finding: The Key to Integration?, Jan. 1997, Behavioral Health Management, Dialog 01858188/9.*

Smith, Delbert D., Distant Doctors, May 1998, Satellite Communications, vol. 22 No. 5, pp. 32–40, Dialog 01626719/9.*

Messmer, Ellen, Video Nets help doctors serve remote areas, Jul. 11, 1994, Network World, vol. 11 No. 28, pp. 18, Dialog 00886955/9.* www.cyberdocs.com.
www.diabeteswell.com.
www.kronos.com.
www.global telemedix.com.
www.ehealthcare.net.
Medweb.med.uci.edu/cources/informatics/resources/ehealth.html.

*Primary Examiner*—Joseph Thomas
*Assistant Examiner*—Carolyn Bleck
(74) *Attorney, Agent, or Firm*—Alberto Q. Amatong, Jr.; The Morris Law Firm, P.C.

(57) ABSTRACT

A system and method for conducting a physician-patient consultation is disclosed wherein the patient is located, at least initially, remotely from the physician. The system includes a first clinic station operable by a physician, a patient station remote from the first clinic station for communicating information relating to the patient, and a second clinic station operable by medical personnel for direct contact with the patient, i.e., conducting a physical examination of the patient. A communications network is also provided which includes a communication link between the first clinic station and the patient station, whereby the fist communication link utilizes an interactive computer network and a second communications link between the second clinic station and the first clinic station. In the method, a first set of patient information is communicated from the patient station to the first clinic station and thus to the physician. A first type of patient information is obtained for the purpose of advancing or firing consultation. A second set of patient information is then gathered by the second clinic station through direct contact with the patient, i.e., direct interview and/or physical examination. Both types or sets of patient information is stored in the computer database and are accessible by the physician station.

16 Claims, 4 Drawing Sheets

U.S. PATENT DOCUMENTS

| | | | |
|---|---|---|---|
| 5,960,403 A | * 9/1999 | Brown | 128/237 |
| 5,961,332 A | * 10/1999 | Joao | 434/236 |
| 5,974,124 A | * 10/1999 | Schlueter et al. | 379/106.02 |
| 5,997,476 A | * 12/1999 | Brown | 600/300 |
| 6,024,699 A | * 2/2000 | Surwit et al. | 600/300 |
| 6,039,688 A | * 3/2000 | Douglas et al. | 600/300 |
| 6,046,761 A | 4/2000 | Echerer | 348/14.01 |
| 6,101,478 A | * 8/2000 | Brown | 705/2 |
| 6,139,494 A | * 10/2000 | Cairnes | 600/300 |
| 6,168,563 B1 | * 1/2001 | Brown | 600/301 |
| 6,208,973 B1 | * 3/2001 | Boyer et al. | 705/2 |
| 6,256,613 B1 | * 7/2001 | Falchuk et al. | 705/2 |
| 6,270,457 B1 | * 8/2001 | Bardy | 600/300 |
| 6,343,271 B1 | * 1/2002 | Peterson et al. | 705/4 |
| 6,418,346 B1 | * 7/2002 | Nelson et al. | 607/59 |
| 6,491,649 B1 | * 12/2002 | Ombrellaro | 600/587 |
| 6,569,093 B2 | * 5/2003 | Iliff | 600/300 |
| 2002/0022975 A1 | * 2/2002 | Blasingame et al. | 705/3 |

* cited by examiner

SYSTEM AND METHOD FOR CONDUCTING A PHYSICIAN-PATIENT CONSULTATION

BACKGROUND OF THE INVENTION

The present invention relates generally to a system and method of communicating information between two or more stations or sites which are located remotely from one another. More particularly, the invention relates to a system and method of communicating information between one or more such stations for the purpose of conducting a physician-patient consultation. In one application, a system and a method are provided which are particularly adapted for use with or over a communications network including the Internet.

The present mode of physician-patient consultation is conducted in a setting wherein the physician meets with the patient face to face. During this meeting, the physician or other medical personnel gathers a variety of information from the patient through interview, retrieval of existing records, physical examination and other information gathering methods. Based on the information gathered, the physician evaluates the patient's condition and may prescribe medication or treatment, refer the patient, provide a diagnosis, and/or direct the patient to another location or person for further gathering of information. It is known to store some of the gathered information in an electronic database such that the physician and other medical personnel may retrieve and review the information during evaluation.

In this traditional setting, a patient typically schedules an appointment with his or her physician's office well in advance of the meeting. In many cases, the patient will take time off from work to visit the physician and will travel to the physician's office or a hospital to meet with the physician. The physician may also direct the patient to other locations for further examination, testing etc. In the end, the patient may visit the physician several times before conclusion of the consultation. Although inefficiencies such as these are associated with existing methods and systems for conducting a physician-patient consultation, these inefficiencies have long been accepted by both patients and physicians.

SUMMARY OF THE INVENTION

It is, therefore, one of multiple objects of the invention to provide an improved system and method for communicating information between a physician and a patient for the purpose of conducting a physician-patient consultation. More particularly, the invention provides such an improved system and method wherein the patient is located, at least initially, remotely from the physician. In this context, such "consultation" may include (but not limited to), among other activities, examination of a patient including obtaining a patient's history, performing an assessment, diagnosis, referring the patient to appropriate medical professionals, prescribing medication or treatment, triaging, or any combination of these and other services or care rendered by a physician or medical professional.

Therefore, in one aspect of the invention, a system and method are provided for conducting a physician-patient consultation. The system includes a first clinic station operable by a physician, a patient station remote from the first clinic station for communicating information relating to the patient, and a second clinic station operable by medical personnel for conducting an examination of a patient. The method includes providing a communications network including a first communication link between the first clinic station and the patient station, whereby the first communications link utilizes an interactive computer network, and a second communications link between the second clinic station and the first clinic station. The physician (or other medical personnel at the first client station) then remotely interviews the patient or patient representative at the patient station (e.g., to gather patient information and to establish a physician-patient relationship) by way of the first communication link such that a first set of patient information is communicated from the patient station to the first clinic station and the physician. Preferably, an Internet link including a web site is provided for this purpose.

The step of remotely interviewing the patient provides for the communication of a certain type or set of patient related information from the patient station to the first clinic station. This first type or set of patient information is obtained for the purpose of advancing or furthering the consultation. This may involve providing written or oral responses to inquiries (e.g., a standardized questionnaire, interactive question and answer, etc.), observation of the patient, transfer of data or, as available technology allows, remote physical examination of the patient. However, it may not be possible, appropriate or desirable to communicate certain patient-related information (a second set of patient information) from a remote site to the physician's clinic station, in order to complete the consultation. It is preferred that this set of patient-related information be obtained upon direct contact with the patient. Among other things, this may involve a person-to-person interview or a physical examination of the patient (by man or machine) or of physical samples provided by the patient.

The method further includes receiving, at the first clinic station, a second set of patient information (i.e., which is not obtained via the remote interviewing step) directly or indirectly from the second clinic station. Preferably, this second set of patient information is obtained at the second clinic station and is communicated to the first clinic station by accessing the communications network and storing the information in a computer database. Accordingly, at the first clinic station, the physician accesses the database and evaluates the patient's condition upon review of both the first and second sets of patient information. The physician may then communicate a diagnosis, referral, prescription, treatment, and the like, to the patient via the first communication link.

In one embodiment of the invention, the step of remotely interviewing the patient precedes the step of receiving the second set of patient information and the method may include the additional step of directing the patient to the second clinic station. In another embodiment, the step of remotely interviewing the patent occurs after the step of receiving the second set of information.

A system for providing a physician-patient consultation according to the invention includes a first clinic station operable by a physician and a patient station accessible by a patient representative (e.g., the patient or a caretaker) and located remotely from the first clinic station. A second clinic station is also provided that is operable by medical personnel (e.g., for interview, physical examination or operating a machine or laboratory for testing, etc.) and adapted for direct contact with a patient to obtain patient information. The inventive system further includes a communications network including a first communications link between the first clinic station and the patient station, wherein the first communications link includes a computer network interface adapted to communicate a first set of patient information from the patient to the physician. In this regard, the first clinic station may be described as a "virtual clinic."

Preferably, this network interface will include an Internet web site particularly adapted for facilitating physician-patient consultation. The communications network also includes a second communication link for communicating the second set of patient information from the second clinic station to the first clinic station, and at least one computer and a computer database accessible by the computer for storing the first and second sets of patient information. The computer database is disposed so as to be accessible by the first clinic station.

Thus, in one aspect of the invention, a computer-implemented network or system is provided which includes at least one computer, a database, and program means executable by the computer for managing the storage, manipulation and/or retrieval of patient information. In particular, the system is adapted to receiving one set of patient information gathered upon remote (e.g., on-line) interview with the patient or patient representative and a second set of patient information gathered by director contact with the patient at a traditional clinic setting. The two sets of patient information are stored in a computer database. At least some of the information is made accessible to a physician(s) for review.

As yet another feature and advantage offered by the invention, a system and method of physician-patient consultation is provided that greatly benefits the patient. The inventive system and method provides improved efficiency and flexibility, and is easy to use. In many applications, the patient saves considerable time and effort because he or she can access the physician clinic without having to schedule an appointment far in advance, and without having to travel to the clinic and then wait to see the physician. In some cases, such flexibility is critical. In other cases, such flexibility and convenience may remove some of the physical and psychological barriers which can discourage or even prevent a person (or animal) from seeking medical help.

The present system and method, and various aspects thereof, are adapted for conducting various types of physician-patient consultation. These include consultation provided by a medical doctor (generalist or specialist), a veterinarian, dentist, psychiatrist and other healthcare professionals.

These and other objects, features, and advantages of the present invention will become apparent to those skilled in the art from the following detailed description of one or more preferred embodiments and the accompanying drawings.

DETAILED DESCRIPTION OF THE DRAWINGS

Figure 1:
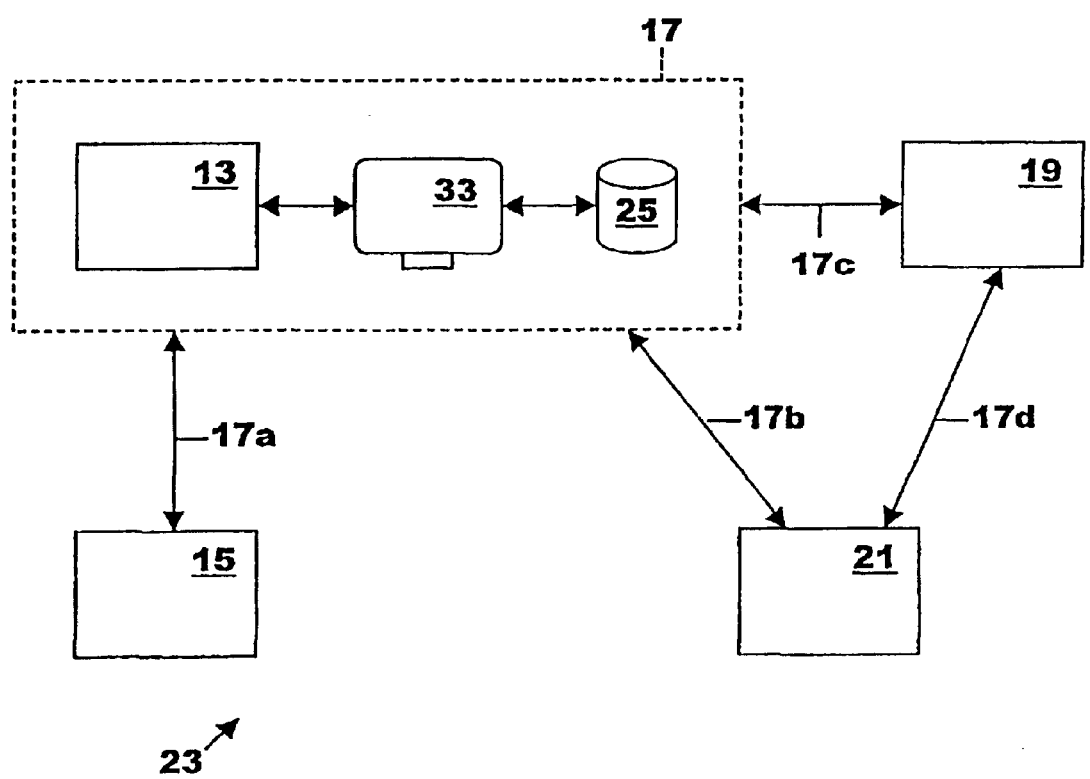
FIG. 1 is a simplified entity relationship diagram embodying the present invention.
Figure 2:
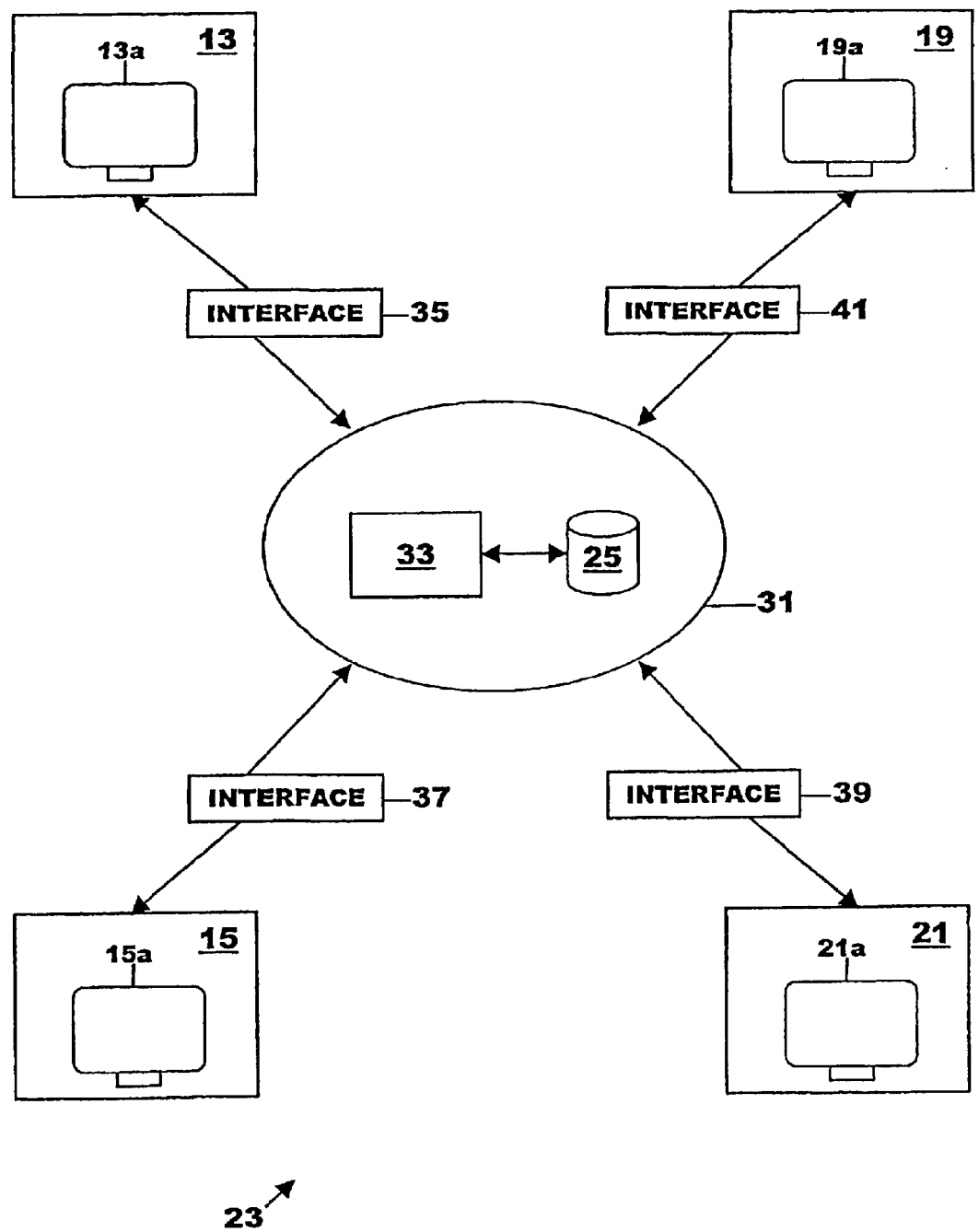
FIG. 2 is a simplified system configuration diagram embodying the invention.

FIGS. 1 and 2 generally illustrates a system entity-relationship diagram and a system configuration diagram, respectively, both embodying various aspects of the present invention. More particularly, the Figures illustrate a system and communications network which are suitable in a method of communicating information between at least one physician and at least one patient, wherein the patient is located, at least initially, remote from the physician. Therefore, a method of conducting a physician-patient consultation is disclosed, which involves the communicating of information relating to the patient from a remote patient site or station to a physician site or station.

In this regard, the physician site may be regarded as a "virtual clinic" or "virtual physician station." In such a setting, the physician consults with the patient but does not have to have direct contact with the patient (i.e., does not meet with the patient in person). This may be distinguished from a "traditional clinic" or "traditional physician station" wherein the patient must be present to meet, in person, with the physician so as to conduct any type of physician-patient consultation.

For purposes of the present description, the system according to the invention may be regarded as generally including the following functional entities: a network hub 17, a patient station 15, a traditional clinic station 19, and, preferably, a third party station 21. The network hub 17 includes a physician clinic station or physician station 13, at least one computer 33, and an electronic database 25 for storing information. Preferably, a program and memory means reside in the computer 33 suitable for management of information that is directed into or out of the computer database 25 and/or stored therein. The network hub 17 is disposed in communication with each of the patient station 15, the traditional clinic station 19, and the third-party station 21. Further, the physician station 13 is disposed in communication with the computer 33 and the database 25 such that the physician clinic station 13 may direct and/or retrieve information from the database 25. As discussed in further detail below, each of the stations 15, 19 and 21 may access, to some predetermined extent, information stored in the database 25.

It should be understood that the computer 33 and the database 25 may reside in the same physical location (i.e., same office) as the physician station 15, and may even be regarded as part of the physician station 15. The term "physician station" can refer to any location(s) at which the physician can perform the one or more steps of the inventive physician-patient method of consultation (e.g., a physician's clinic), and should not be limited to specific hardware.

The network 23 preferably includes communications link 17a which may include any suitable type of Internet access communication devices or networks. Also, communications links 17b, 17c, and 17d are provided to interconnect the stations 19, 21 and network hub 17. Preferably, these communications links will include an interactive computer network utilizing terminals and traditional data transmission lines, but can also consist of or include telephonic means, facsimile means, video conferencing devices and the like.

Although the present invention is particularly adapted for utilization of an interactive computer network such as the Internet, it shall be apparent to one skilled in the art, given the present disclosure, that the inventive communication network 23 is also adapted for utilization of other communications networks and devices including Intranet systems, other client-server networks, personal digital assistant devices (e.g., a palm pilot), and the like. Similarly, the inventive system and method is equally adapted to other communication environments and in respect to entities other than those described in detail herein. Accordingly, the systems and methods described herein are provided for exemplary purposes only and is not intended to limit the scope of the invention.

In one aspect of the invention, a system is provided that is particularly adapted to communicating information from a patient station 15 to a physician station 13 via communications link 17a wherein the patient is remotely located from the physician. The second clinic station 19 is preferably a traditional clinic setting that may be affiliated with or predesignated by the physician station 15. The clinic station 19 is "traditional" in the sense that, for purposes of the present inventive system and method, the patient must physically present himself or herself at the clinic or present physical samples thereto for physical examination (including treatment) by man or machine. Examples of typical clinic stations which may be affiliated with a physician station of the invention include, but is not limited to, those associated with a traditional doctor's office (generalist or specialist), pharmacy, medical laboratory, physical therapy center, imaging center or hospital.

The patient station 15 may be any communication site designated by the physician station 13. Alternatively, the patient station 15 may be located in the patient's home, work or other location. In any case, the patient station 15 may be any physical location(s) at which one can remotely communicate with the physician station 13. In such a setting, communication of information may be effected by the patient or a patient representative (e.g., a nurse, relative, caretaker, etc.) acting as an intermediary between the patient and physician. However, as used heretofore and in the claims, the term "patient representative" can mean the patient or an individual other than the patient, and the term "patient" can mean the patient or an individual other than the patient (except, of course, wherein a physical examination of the "patient" is required).

FIG. 2 depicts a preferred system configuration suitable for the inventive method and embodying various aspects of the invention. Generally, the communications network or system 23 is an Internet-based system, which allows for interconnection and communication between each of the stations 13, 15, 19 and 21. The system 23 includes a computer system or network 31 having one or more servers 33 (for database storage and Internet access), a storage database 25 and program means executable to manage information directed to or retrieved from the database 25. Further, the computer system 31 is adapted to support a website that allows for interaction between the physician clinic station 13 and the patient station 15. The components of the computer system 31 may be physically located in any one of the entities or another site.

The physician station 13 is equipped with a terminal 13a or other network access device (including a personal digital assistant device) operable by the physician or another person to access the Internet and the computer network 31. A user interface 35 including a web page is preferably provided for operation with the terminal 13a. Preferably, the physician station 13 is equipped with most, if not all, of the hardware which constitutes the computer system 31, in addition to terminal 13a and traditional medical equipment and personnel.

Similarly, the patient station 15 includes a terminal 15a or other access device operable with a user interface 37 to access the network 31. The patient station 15 may comprise any location and/or hardware accessible by the patient, but which includes the terminal 15a for operating the user interface 37 and accessing the computer network 31. In one application, the terminal 15a is a personal computer operable by the patient at his or her residence, work or while traveling.

The traditional clinic station 19 preferably includes or is equipped with a terminal 19a operable with a user interface 41 for accessing the website and the computer system 31. The traditional clinic station 19 is preferably a predesignated clinic having a terminal 19a for accessing the website. It is understood, however, that the traditional clinic station may be a clinic not historically or traditionally affiliated with the physician clinic station 13. Moreover, the communications link between such a traditional clinic station 19 and the physician station 13 may be provided by traditional means including telephone, facsimile and the like, in addition to or in lieu of interface 41.

As shown in FIG. 2, the communications network 23 can also include a third-party station 21 such as a billing/insurer entity. The third-party station 21 is equipped with a terminal 21a operable with a user interface 39 for accessing the computer network 31 and website. Alternatively, the communications link between the third-party station 21 and the other stations may be provided by traditional means including telephone, facsimile and the like, in addition to or in lieu of interface 39. Preferably, the third-party station, and the other station discussed above are equipped to access at least some of the information which may be stored in the database 25 and, in some cases, for directing information for storage therein.

In one regard, the inventive method may be initiated by a step of providing communication between the physician station 13 and the patient station 15 and remotely interviewing the patient via the communications link 17a (step 101). As discussed above, communication may be established when the patient accesses the website of the computer system 23 and is linked to a patient-user web page (i.e., user interface). The website may be include a secured portion into which a patient-user enters upon successful logon and verification. For first time users, a particular web page may be provided which requires the patient-user to undertake certain registration procedures and to enter preliminary personal information. Unique patient-user identifiers can be used to verify the user (or initial and/or subsequent visits) and also to facilitate access to patient-user information already stored in the computer database 25.

The web page may include a questionnaire for the patient to fill out, and electronic e-mail capabilities to submit additional information and questions. An online chat room may be provided for corresponding with the physician or other medical personnel. Further, this interaction between the patient station 15 and the physician clinic station 13 may be supplemented by telephonic communication, video conferencing and facsimile transmission. Further yet, known remote physical examination technology may be incorporated into the communications network and used to remotely communicate some information (e.g, blood pressure, temperature, height, weight, blood sugar level, etc.) to the physician station 13. For purposes of the present description of the invention, and the claims which follow, any of the above forms of communication or interaction between the physician and patient constitutes the physician "remotely interviewing" the patient and the communication of patient information from the patent (i.e., patient station) to the physician (i.e., physician clinic station).

Patient related information ("patient information") communicated by way of the above modes include patient's history (e.g., medical, surgical, family, social, psychological, personal, etc.), medications, current chief complaints, vital sign data, physical examination data, and ancillary data. Such information may also include responses to any therapeutic modalities employed in the patient treatment. Other patient information will include name, date of birth, address, telephone number, facsimile contact, email, etc. It is intended that the term "information" encompass information and data in a variety of forms, including raw information and data representing raw information which is stored in electronic form. Upon collection of this information, it is possible that the physician may be able to assess the patient's condition, to diagnose, triage and/or treat the patient online (i.e., over the virtual clinic). In such a case, the interaction between patient and physician (i.e., consultation) terminates, and the patient or third-party provider is subsequently billed for the services provided.

However, in certain situations, information which is necessary for the proper assessment, diagnosis and/or treatment (i.e., consultation) of the patient may not be complete and may not be properly obtainable via the remote interviewing steps. To gather this information may require the patient to present himself or herself or physical samples to medical personnel. Whereas, Category A patient information includes information that can be or is properly obtainable by remote interview, Category B information includes those types of information which the physician deems cannot be properly obtainable by remote interview (given available technology). Typically, Category B patient information includes measurements not obtainable without direct contact with the patient and results of physical examination requiring the physician's close-up examination and judgment, and/or gathering of ancillary data resulting from imaging studies, laboratory work, therapeutic and interventional procedures and modalities, etc.

Patient information gathered by remote interview is subsequently stored in the datebase 25 in such a manner that it is readily accessible by patient name, patient identifier, date of remote interview and/or other indexing means. Some of this information (which are of Category A) will be transferred directly into the database 25 upon entry by the patient on the appropriate web page. Other information may be directed to or originate from the physician clinic 13.

In a subsequent step of the inventive method, the patient is directed to the traditional clinic station 19 (step 102b). The physician or physician station 13 may contact the responsible party in the traditional clinic station 19 regarding the physical examination of the patient (e.g., to give specific instruction) (step 102a). At the traditional clinic station 19, medical personnel will interview the patient directly and gather additional patient information (e.g., as directed by the physician). Additional information is, therefore, obtained from the patient (which could include information that may also be classified as Category A information, as well as Category B information). Additional patient information gathered may include patient history, vital signs, physical examination results, laboratory work, radiology data, interventional studies, physical therapy data, electrical conduction studies and results of specialist consultation, etc.

The patient information collected at the traditional clinic station 19 is directed to the computer network 23 (step 104) and stored in the database 25. This information is, therefore, accessible by the physician station 13. It should be noted that, in some applications, the traditional clinic station 19 will have two-way access to the computer network 23 and database 25. Thus, it is contemplated that the traditional clinic station 19 may retrieve patient information already stored in the database 25 (step 153). For example, at least some of the Category A patient information obtained in the remote interviewing step will be directed into computer system 23 for storage in the database 25 and will be useful in the examination of the patient in the traditional clinic station 19. Further, additional patient information originating from the physician station 13 or derived from gathered patient information, including medical instructions from the physician, may be stored in the database 25 for communication to the traditional clinic station 19.

Accordingly, one result of the remote interview by the physician and information gathering by the traditional clinic station 19 is a body of information that is integrated into a database 25 for the benefit of various entities, including the physician station 13. The database includes both Category A and Category B patient information. Thus, in one aspect of the invention, the system and method provides such an integrated patient information database which is accessible and reviewable by a physician for consultation. It will be further apparent that such an integrated patient information database may be created for a plurality of patients, and adapted to receive additional and future patient information. Moreover, such an integrated patient information database is adapted for use with activities other than physician-patient consultation. For example, patient information contained in the database may be used in non-consultation tasks and activities, effected, at least partly, through the computer system 23. These include administrative tasks such as billing, patient scheduling, and general correspondence between patient, physician station, traditional clinic stations, and/or third-party billing/insurer entities.

Figure 3:
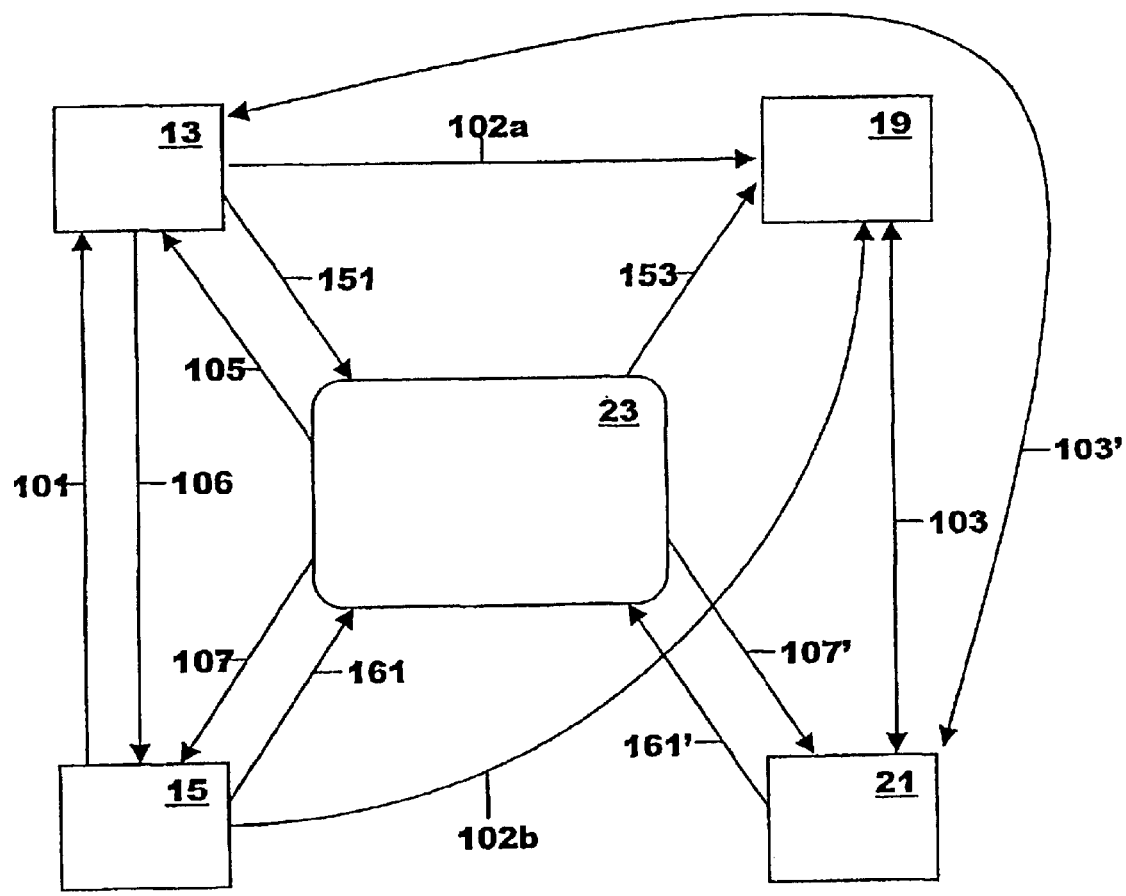
FIG. 3 is a schematic flow chart illustrating a system and method according to the invention.

Referring again to the flow chart of FIG. 3, in a subsequent step, the physician station 13 retrieves patient information from the database 25 by operation of the terminal 13a and access to computer system 23 (step 105). The physician at the physician station 13 can review both Category A and Category B information (previously gathered or recently gathered) for purposes of patient evaluation. The result of this evaluation may be communicated to the patient via the communications link 17a and patient station 15 (step 106) and to complete the physician-patient consultation. However, additional remote interviewing of the patient may be conducted via the communications link 17a prior to or subsequent to evaluation, as the case requires.

In one variation of the inventive method, the traditional clinic station 19 and/or the physician station 13 is adapted to communicate electronically with a third-party station 21 (step 103, 103'). In this way, the traditional clinic station 19 and/or physician station 13 may contact a billing/insurer entity to verify the patient's benefits. Such verification may be communicated, upon request, by the billing/insurer entity to the traditional clinic station 19 and/or physician station 13. It is contemplated that, in some applications, such verification be obtained by accessing the third party station directly (e.g., a computer system and/or database). The traditional clinic station 19 and/or physician station 13 may also communicate with the third-party station 21 to request and receive preauthorization for a medical procedure (e.g., prescription of medication, referral to a specialist, testing (to gather ancillary data), therapies, surgeries, etc.). Moreover, the traditional clinic station 19 and/or physician station 13 may communicate with the third-party station 21 for billing collection activity. For any of the above communications between the traditional clinic station 19 and/or physician station 13 and the third-party station, the third-party station 21 may access the database 25 to retrieve and review information concerning the patient.

In yet another variation of the inventive method, the computer network 23 (and software provided therefor) is adapted to automatically bill the patient after services are rendered. Such a billing step may be effected, at least partially, online utilizing the communications network 23 (step 107). Alternatively, such a billing step may be directed to a third-party billing station 21 (step 107'). In either case, the communications network 23 may be utilized to confirm that funds have been secured for the billed amounts and then the patient's account may be marked as closed or current. Furthermore, the patient and/or the third-party entity may, in some applications, access the computer network 23 and database 25 to review information regarding the patient's account (step 161, 161').

The inventive system and method is further adapted to allow the patient to follow up online, after the initial consultation. In such a follow-up consultation, the physician will have, at his or her disposal, patient information regarding the previous consultation as well as other previously stored Category A and B patient information. Alternatively, the patient may choose to have the follow-up consultation conducted in a traditional clinic setting.

As discussed previously, two types of patient information are obtained through employment of the inventive method-Category A and Category B. These information types are primarily distinguished by the method by which these are obtained in the inventive method. It is understood that Category B information may include patient information not otherwise properly obtainable by the remote interviewing step. In any case, one aspect of the invention is a data model which provides storage and access to both categories of information. Further, the data model may be referred to as including four sets of patient-related information. The following tables provide examples of some of the patient information gathered in the inventive method:

| (1) Patient Administrative Information | (2) Patient History | (3) Patient Physical Examination (incl. ancillary data) | (4) Payment |
|---|---|---|---|
| Name | Chief Complaint | Vital signs (age, height, weight, blood pressure, pulse, respiratory rate, temperature, etc.) | Credit Card or Debit Card |
| Date of Birth | Past medical history | Physical Exam (HEENT, heart, lung, abdomen, extremities, neurological, etc.) | Check (electronic or paper) |
| Address | Past surgical history | Laboratory work (chemistries, cell blood counts, lipid panels, etc.) | Third party medical insurance |
| Telephone | Medication | Radiology data (Xrays, CTs, MRIs, ultrasounds) | Third Party Guarantor |
| Facsimile | Allergies | Interventional studies and procedures (surgeries, biopsies, interventional radiology and cardiology including coronary catherizations, discograms, etc.) | |
| Email address | Family history | Physical therapy data | |
| Unique Patient Identifiers | Social history | Electrical conduction studies (EKGs, EMGs, EEGs) | |
| | Review of systems | Results of specialist consultation | |

Typically, types (1), (2) and (4) patient information are obtained during the remote interview and stored in the database 25 soon after, along with patient information originating from the physical client station 13 (e.g., patient account number, unique patient identifier, treating physician, etc). Some of type (3) patient information may also be obtained during the remote interview. For example, vital signs, physical examination data and records/documents in the possession of the patient may be obtained during the remote interview. With emerging medical technology, it is probable that more and more physical examination information will become obtainable via the remote interview. Accordingly, the inventive method shall not be limited to acquisition of specific types of patient information. The distinction made between the Category A and B information relies on how the information is actually acquired in the consultation or, alternatively, how the physician prefers to obtain the information or deems is the proper method of obtaining the patient information considering available technological capabilities (both software and hardware).

Figure 4:
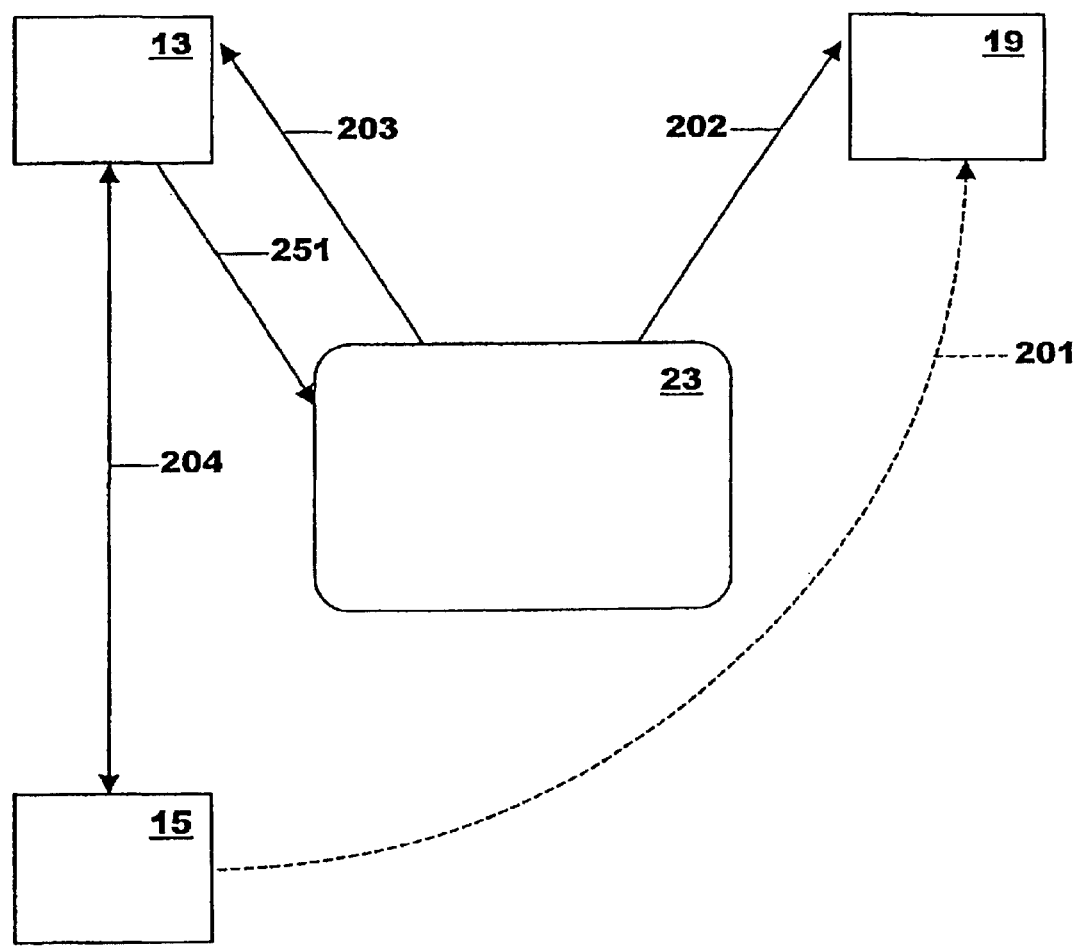
FIG. 4 is a schematic flow chart illustrating an alternative system and method of the invention.

Now referring to FIG. 4, an alternative method for conducting a physician-patient consultation, according to the invention, may be initiated by the patient visiting a traditional clinic station 19 (step 201). At the traditional clinic station 19, medical personnel interviews the patient and gathers patient information, including Category A and B patient information. Typically, the traditional clinic station 19 will access the computer database 25 to review previously gathered patient information (including preliminary administrative data and medical history) if such patient information has already been gathered and stored.

Patient information gathered by the traditional clinic station 19 is then directed to the computer system 23 for storage in the database 25 (step 202). Upon entry into the database 25, this information becomes accessible to a physician at a physician clinic station 13 incorporated into the system 23 (e.g., a virtual clinic). Data may be downloaded, reviewed or otherwise communicated to the physician at the physician station 13 (step 203). Thus, the physician at the physician station 13 can benefit from the stored information for the proper assessment, diagnosis and treatment of the patient when that patient is presented online in the future (step 204). In this way, the physician can attend to management of acute complaints or continue management of chronic disease (should the patient choose to see the physician via the virtual clinic as opposed to a traditional clinic setting). The physician may also gather and store additional information (step 251) in the computer database.

It should be noted that the hardware and software required for employment of the alternative method may be the same as those employed by the previously described embodiment (see FIG. 2). It should also be noted that Category B information may be gathered at a traditional clinic station 19 that may or may not be remote from the physician station 13 (the two stations could physically coincide), and then communicated to the physician station 13 so that the physician can perform an evaluation based, at least partially, on the gathered patient information.

The systems and methods described above are particularly adapted for a physician-patient consultation. However, it will be apparent to one skilled in the art, upon reading the description and viewing accompanying drawings, that certain aspects of the systems and methods are also applicable in other communications environments and other consulting relationships. Moreover, it should be noted that the inventive system and method are applicable in many other professional-client relationships including those involving a Medical doctor, a dentist, a veterinarian, psychiatrist, other medical professionals, and other professionals.

The foregoing description is presented for purposes of illustration and description, and is not intended to limit the invention to the forms disclosed herein. Consequently, variations and modifications to the systems and methods commensurate with the above teachings and the teachings of the relevant art are within the scope of the invention. These variations will readily suggest themselves to those skilled in the relevant art and are encompassed within the spirit of the invention and the scope of the following claims. Moreover, the embodiments described are further intended to explain the best mode for practicing the invention, and to enable others skilled in the art to utilize the invention in such, or other, embodiments, and with various modifications required by the particular applications or uses of the invention. It is intended that the appended claims be construed to include alternative embodiments to the extent that it is permitted by prior art.

What is claimed is:

1. A method for conducting a physician-patient consultation, said method comprising the steps of:

providing a first clinic station operable by a physician, a patient station remote from the first clinic station for communicating information relating to the patient, and a second clinic station operable by medical personnel to conduct a patient examination;

providing a communications network including a first communication link between the first clinic station and the patient station, whereby the first communications link utilizes an interactive computer network, and a second communications link between the second clinic station and the first clinic station;

remotely interviewing the patient via the first communications link to communicate a first set of patient information from the patient station to the first clinic station and the physician;

storing the first set of patient information in the database, such that the set of information is accessible by the first clinic station;

at the fist clinic station, determining a second set of patient information distinct from the first set of patient information as being necessary to complete the consultation;

directing the patient to the second clinic station for examination by medical personnel and obtaining the second set of patient information;

storing the second set of patient information in the database such that both the first and second sets of information are accessible by the first clinic station;

at the first clinic station, receiving the second set of patient information, wherein the second set of patient information is obtained by examination of the patient at the second clinic station and is communicated to the first clinic station via the second communications link;

at the first clinic station, evaluating the patient's condition upon review of the first and second sets of patient information; and from the first clinic station and via the first communications link, communicating a consultation service selected from the group of consultation services consisting of: providing a diagnosis; prescribing a medication; prescribing a treatment; and combinations thereof;

wherein the communications network includes an Internet website accessible by the patient station, and wherein said step of remotely interviewing the patient includes communicating information from the patient station to the first clinic station via the website; and wherein said first set of patient information excludes information obtainable only via direct contact with the patient, and said second set of patient information includes patient information obtainable only by direct contact with the patient.

2. The method of claim 1, wherein the step of receiving the second set of patient information precedes the remote interviewing step.

3. The method of claim 1, wherein the communications network further includes a third-party station operable by a responsible third-party entity, said method further including the step of communicating patient information between the third-party entity and at least one of the first clinic station and the second clinic station by utilizing the communications network.

4. The method of claim 3, wherein the third-party entity is an insurer and wherein said step of communicating information between the third-party entity and the first client station includes requesting verification and preauthorization from the insurer.

5. The method of claim 3, further comprising the step of billing the third-party entity via the communications network.

6. The method of claim 1, wherein said communications network is an interactive computer network including a server station and an information database interconnected with the server station, and a client station at each of the patient station, first clinic station, and second clinic station.

7. The method of claim 1, further comprising the step of communicating, via the first communications link, a physician's evaluation from the first clinic station to the patient station, after the evaluating step.

8. The method of claim 1, wherein said second set of patient information is obtained by direct physical examination and not obtainable by the remote interviewing step.

9. The method of claim 1, wherein the second set of patient information includes information not obtainable by the remote interviewing step but necessary for the evaluating step.

10. The method of claim 1, wherein the remote interviewing step includes communicating information selected from the group of types of patient information consisting of: administrative information including patient name, date of birth, address and contact numbers, patient history including allergies, medical history, medication, and family history, and combinations thereof; and wherein the step of receiving a second set of patient information includes receiving the types of information selected from the group of types of patient information consisting of: laboratory data, radiology data, laboratory work data, information gathered from interventional studies, information gathered from electrical conduction studies, information gathered from other physical examinations, and combinations thereof.

11. A system for providing a physician-patient consultation, said system comprising:

a first clinic station operable by a physician;

a patient station accessible by a patient for communicating a first set of patient information, said patient station being remote from said first clinic station;

a second clinic station operable by medical personnel, said second clinic station being adapted for direct contact with a patient to obtain a second set of patient information; and a communications network including a first communications link between said first clinic station and said patient station, said first communications link including a computer network interface adapted to communicate said first set of patient information from said patient station to said first clinic station, a second communication link for communicating said second set of patient information from said second clinic station to said first clinic station, and at least one computer and a computer database accessible by said computer for storing said first and second sets of patient information, said computer database being accessible by said first clinic station and adapted to receive said first set from said first communications link for storage in said computer database and to receive said second set from said second communications link for storage in said computer database, wherein said second set of patient information is patient information selected from the group consisting of: vital signs, physical examination results, radiological information, results of interventional studies, physical therapy data, electrical conduction study data specialist consultation data, and combinations thereof.

12. The system of claim 11, wherein said communications network includes an interactive computer network providing at least said first communications link, said interactive computer network being interconnected with said at least one computer.

13. The system of claim 12, wherein said network interface includes a web site accessible by said patient station to communicate said first set of patient information.

14. The system of claim 12, wherein said communications network includes a terminal at each of said patient station, said first clinic station, and said second clinic station, each said terminal being adapted to access the website and to access said computer database for communicating patient information therebetween.

15. The system of claim 11, further comprising a third party billing station and a third communications link between said communications network and said third party billing station, said third party communications link being adapted to communicate information relating to the patient's account between said communications network and said third party billing station.

16. The system of claim 11, wherein said computer database is adapted to integrate said first and second sets of patient information in one accessible memory storage area.

* * * * *